(12) United States Patent
Buchman

(10) Patent No.: US 7,922,701 B2  
(45) Date of Patent: Apr. 12, 2011

(54) CATHETER CLEANING DEVICES

(76) Inventor: Alan L. Buchman, Winnetka, IL (US)

( * ) Notice: Subject to any disclaimer, the term of this patent is extended or adjusted under 35 U.S.C. 154(b) by 229 days.

(21) Appl. No.: 11/706,517

(22) Filed: Feb. 14, 2007

(65) Prior Publication Data

US 2008/0132880 A1 Jun. 5, 2008

Related U.S. Application Data

(60) Provisional application No. 60/774,708, filed on Feb. 17, 2006.

(51) Int. Cl.
*A61M 5/14* (2006.01)

(52) U.S. Cl. .......... 604/256; 604/533; 604/905

(58) Field of Classification Search .......... 604/167.01–167.06, 199, 246–251, 604/256, 263, 267, 533–539; 422/292, 294, 422/300; 401/132–135, 9–12; 15/104.001, 15/104.03, 104.04, 104.94, 104.93
See application file for complete search history.

(56) References Cited

U.S. PATENT DOCUMENTS

| | | | | |
|---|---|---|---|---|
| 4,334,551 A | * | 6/1982 | Pfister | 137/614.03 |
| 4,340,052 A | * | 7/1982 | Dennehey et al. | 604/317 |
| 4,432,759 A | * | 2/1984 | Gross et al. | 604/411 |
| 4,432,764 A | | 2/1984 | Lopez | |
| 5,071,411 A | * | 12/1991 | Hillstead | 604/246 |
| 5,375,589 A | | 12/1994 | Bhatta | |
| 5,383,851 A | | 1/1995 | McKinnon et al. | |
| 5,554,135 A | | 9/1996 | Menyhay | |
| 5,630,813 A | * | 5/1997 | Kieturakis | 606/46 |
| 5,743,892 A | * | 4/1998 | Loh et al. | 604/537 |
| 6,753,306 B2 | * | 6/2004 | Simpson | 510/439 |
| 6,916,051 B2 | * | 7/2005 | Fisher | 285/373 |
| 2003/0144647 A1 | * | 7/2003 | Miyahara | 604/523 |
| 2006/0293559 A1 | * | 12/2006 | Grice et al. | 600/102 |
| 2007/0112333 A1 | | 5/2007 | Hoang et al. | |
| 2007/0148432 A1 | * | 6/2007 | Baker et al. | 428/304.4 |
| 2008/0039803 A1 | * | 2/2008 | Lynn | 604/256 |

FOREIGN PATENT DOCUMENTS

GB 2 073 893 A 10/1981

OTHER PUBLICATIONS

Arduino et al., "Microbiologic evaluation of needleless and needle-access devices," *Am. J. Infect. Control.* 26:377-380 (1997).
Arnow et al., "Consequences of intravascular catheter sepsis." *Clin Infect Dis.* 16:778-784 (1993).
Bouza et al., "A needleless closed system device (CLAVE) protects from intravascular catheter tip and hub colonization: a prospective randomized study." *J. Hosp. Infect.* 54:279-287 (2003).
Brismar et al., "Bacterial contamination of intravenous line side ports of different designs." *Clin. Nutr.* 6:31-33 (1982).

(Continued)

*Primary Examiner* — Kevin C Sirmons
*Assistant Examiner* — Laura C Schell
(74) *Attorney, Agent, or Firm* — McDermott Will & Emery LLP

(57) ABSTRACT

The present invention provides catheter cleaning devices that are effective at reducing microbial contamination of a catheter port entry. For example, the invention provides a catheter, a catheter cleaning device and a catheter cleaning injection port cap, each of which reduces potential microbial contamination at a catheter port entry.

21 Claims, 8 Drawing Sheets

OTHER PUBLICATIONS

Casey et al., "A randomized, prospective clinical trial to assess the potential infection risk associated with the PosiFlow needleless connector," *J Hosp. Infect.* 54:288-293 (2003).

CDC. "Guidelines for the prevention of intravascular catheter-related infections," *MMWR* 51(10), 1-29 (2002).

CDC. "National Nosocomial Infections Surveillance System (NNIS) report, data summary from Oct. 1986-Apr. 1998, issued Jun. 1998." *Am. J. Infect. Control.* 26:522-533 (1998).

Chaiyakunapruk et al., "Chlorhexidine compared with povidone-iodine solution for vascular catheter-site care: A meta-analysis," *Ann. Intern. Med.* 136:792-801 (2002).

Danzig et al., "Bloodstream infections associated with needleless intravenous infusion system in patients receiving home infusion therapy." *JAMA* 273:1862-1864 (1995).

De Cicco et al. "Source and route of microbial colonization of parenteral nutrition catheters." *Lancet* 2:1258-1261 (1989).

Digiovine, "The attributable mortality and costs of primary nosocomial blood stream infections in the intensive care unit." *Am. J. Respir. Crit. Care Med* 160:976-981 (1999).

Do et al., "Bloodstream infection associated with needleless device use and the importance of infection-control practices in the home health care setting," *J. Infect. Dis.* 179:442-448 (1999).

Forse et al., "Staphylococcus epidermidis: An important pathogen," *Surgery* 86:507-514 (1979).

Garland et al., "A randomized trial comparing povidone-iodine to a chlorehexidine gluconate-impregnated dressing for prevention of central venous catheter infections in neonates." *Pediatrics* 107:1431-1437 (2001).

Inoue et al., "Prevention of catheter-related sepsis during parenteral nutrition: effect of a new connection device." *JPEN* 16:581-585 (1992).

Kellerman et al., "Bloodstream infections in home infusion patients: the influence of race and needleless intravascular access devices." *J. Pediatr.* 129:711-717 (1996).

Kluger and Maki, "A meta-analysis of the risk of intravascular device (IVD)-related blood stream infection (BSI) based on 223 published prospective studies" *In: Abstracts of the 39th Interscience Conference on Antimicrobial Agents and Chemotherapy.* San Francisco, CA: American Society for Microbiology, 514, p. 647 abstract 1913 (1999).

Linares et al., "Pathogenesis of catheter sepsis: a prospective study using quantitative and semi-quantitative cultures of catheter hub and segments." *J. Clin. Microbiol.* 21:357-360 (1985).

Little and Palmer, "Central line exit sites: which dressing?" *Nursing Standard* 12:42-44, (1998).

Llop et al., "Colonization and bacteremia risk factors in parenteral nutrition catherization," *Clin. Nutr.* 20:527-534 (2001).

Maki et al., "Prospective, randomized, investigator-masked trial of a novel chlorhexidine-impregnated dressing (Biopatch) on central venous and arterial catheters (abstr)." *Crit. Care Med.* 28:A42 abstract 50 (2000).

Maki et al., "A prospective, randomized trial of a 1% chlorhexidine-75% alcohol tincture vs. 10% povidone-iodine for cutaneous disinfection and dollow-up site care with central venous and arterial catheters (abstr)." *Crit. Care Med.* 28:A42 abstract 52 (2000).

Merlino et al., "In vitro quantitative model of catheter infection during simulated parenteral nutrition," *J. Clin. Microbiol.* 26(9):1659-1664 (1988).

Mermel, "Correction: Catheter related bloodstream infections." *Ann. Intern. Med.* 133:395 (2000).

Mermel, "Prevention of intravascular catheter-related infections." *Ann. Intern. Med.* 132:391-402 (2000).

Moro et al., "Risk factors for central venous catheter-related infections in surgical and intensive care units." *Infect. Control Hosp. Epidemiol.* 15:253-264 (1994).

Raad and Darouiche, "Prevention of infections associated with intravascular devices," *Curr. Opin. Crit. Care* 2:361-365 (1996).

Rello et al., "Evaluation of outcome of intravenous catheter-related infections in critically ill patients." *Am J. Respir Crit. Care Med.* 162:1027-1030 (2000).

Rupp et al., "Effect of a second-generation venous catheter impregnated with chlorhexidine and silver sulfadiazine on central catheter-related infections: a randomized, controlled trial," *Ann. Intern. Med.*, 143(8):570-580 (2005).

Saint, "Prevention of Intravascular Catheter-Related Infections," AHRQ Publication No. 01-E058, Chapter 16, Jul. 2001. Agency for Healthcare Research and Quality, Rockville, MD. http://www.ahrq.gov/clinic/ptsafety/chap16a.htm.

Salzman and Rubin, "Relevance of the catheter hub as a portal for microorganisms causing catheter-related bloodstream infections," *Nutrition* 13:15S-17S (1997).

Segura et al., "In vitro bacteriological study of a new hub model for intravascular catheters and infusion equipment," *J. Clin. Microbiol.* 27:2656-2659 (1989).

Segura et al., "A clinical trial on the prevention of catheter-related sepsis using a new hub model." *Ann. Surg.* 223(4):363-369 (1996).

Segura et al., "Assessment of a new hub design and the semiquantitative catheter culture method using an in vivo experimental model of catheter sepsis." *J Clin. Microbiol.* 28:2551-2554 (1990).

Sitges-Serra and Linares, "Bacteria in total parenteral nutrition catheters: where do they come from?" *Lancet* 1:531 (1983).

Sitges-Serra et al., "Hub colonization as the initial step in an outbreak of catheter related sepsis due to coagulase negative staphylococci during parenteral nutrition." *J Parenter. Enteral Nutr.* 8:668-672 (1984).

Sitges-Serra et al., "Catheter sepsis: the clue is the hub," *Surgery* 97:355-357, (1985).

Sitges-Serra, "Strategies for prevention of catheter-related bloodstream infections," *Support Care Cancer* 7:391-395 (1999).

Soufir et al., "Attributable morbidity and mortality of catheter-related septicemia in critically ill patients: a matched, risk-adjusted, cohort study," *Infect. Control. Hosp. Epidemiol.* 20:396-401 (1999).

Stotter et al., "Junctional care: the key to prevention of catheter sepsis in intravenous feeding," *J Parenter. Enteral Nutr.* 11:159-162 (1987).

Tan et al., "Molecular epidemiology of coagulase-negative Staphylococcus blood isolates from neonates with persistent bacteremia and children with central venous catheter infections," *J. Infect. Dis.* 169:1393-1397 (1994).

Valles et al., "Nosocomial bacteremia in critically ill patients: a multicenter study evaluating epidemiology and prognosis." *Clin. Infect Dis.* 24:387-395 (1997).

"Antibiotic-Coated Central Venous Catheters Reduce Bacterial Infection in Cancer Patients," http://patient.cancerconsultants.com/news.aspx?id=35266 (Feb. 10, 2006).

"Additional InVision-Plus® Neutral™ Product Features and Benefits", Rymed Technologies, Inc., (2006). http://www.rymedtech.com/html/body_features_benefits.htm.

Israeli Office Action, with English translation, issued in Israeli Patent Application No. 193493, mailed Aug. 26, 2010.

\* cited by examiner

CATHETER CLEANING DEVICES

This application claims the benefit of priority of application Ser. No. 60/774,708, filed Feb. 17, 2006, the entire contents of which is incorporated herein by reference.

This application relates generally to the field of medicine and more specifically to catheter devices.

BACKGROUND OF THE INVENTION

Central venous catheters (CVCs) are indispensible devices for medical practice, particularly among critically ill patients, cancer patients, and those that receive intravenous feeding. These devices allow for the rapid infusion of concentrated medications, fluids, or blood products that can otherwise not be administered via a standard intravenous catheter inserted into a peripheral extremity vein. Although such catheters supply necessary vascular access, they also put the patient at risk for significant infection, which can be life-threatening.

There are an estimated 3 million CVCs inserted each year in the USA and 200,000 in Great Britain (Little and Palmer, *Nursing Standard* 12:42-44, 1998). In the USA, such catheters remain in place for an estimated 15 million catheter days (1 catheter in 1 patient for 1 day=1 catheter day) in ICUs alone (Mermel, *Ann. Intern. Med.* 132:391-402 (2000). Catheter-related bloodstream infection is the most frequent cause of hospital-acquired bacteremia (Valles et al. *Clin. Infect. Dis.* 24:387-395 (1997). 80,000-400,000 central venous catheter (CVC)-related bloodstream infections (CRBI) occur in the USA annually, hospital stay is prolonged by an average of a week, and 2,400-60,000 patients die (Mermel, *Ann. Intern. Med.* 132:391-402 (2000); Raad and Darouiche, *Curr. Opin. Crit. Care* 2:361-3651996; Arnow et al., *Clin. Infect. Dis.* 16:778-784 (1993); CDC, National Nosocomial Infections Surveillance System (NNIS) report, data summary from October 1986-April 1998, issued June, 1998. *Am. Infect. Control* 26:522-533, (1998); Digiovine et al., *Am. J. Respir. Crit. Care Med.* 160:976-981 (1999); Rello et al., *Am. J. Respir. Crit. Care Med.* 162:1027-1030 (2000); Soufir et al., *Infect. Control Hosp. Epidemiol.* 20:396-401 (1999); Kluger and Maki, Abstracts of the 39th Interscience Conference on Antimicrobial Agents and Chemotherapy. San Francisco, Calif.: American Society for Microbiology, 514 (1999)). Estimates of the annual cost of caring for the CVC-related infections in these patients ranged from $296 million to $2.3 billion in 2000 (Mermel, *Ann. Intern. Med.* 133:395 (2000)). The use of needleless catheter devices has been associated with an increased risk for bloodstream infection (Kellerman et al., *J. Pediatr.* 129:711-717 (1996); Do et al., *J. Infect. Dis.* 179:442-448, (1999)).

Most catheter-related bloodstream infections (CRBI) associated with the use of long-term catheters (>10 days) stem from endoluminal contamination and subsequent colonization of the catheter hub. The hub may become contaminated when microorgansims are present on the external hub surface from contact with the patient's skin, tracheostomy secretions, wounds, ostomy and feces, and the like, or from transfer to the hub surface from the physician or nurse manipulating the catheter (Cicco et al., *Lancet* 2:1258-1260 (1989)). Most episodes of CRBI are caused by coagulase negative staphylococci, *Staphylococcus aureus*, enterococci species, *Klebsiella pneumonia, Escherichia coli,* and *Candida* species (CDC. Guidelines for the prevention of intravascular catheter-related infections. *MMWR* 51:1-29, (2002)).

The catheter hub (junction of the catheter and intravenous tubing) has been identified as the primary source of CRBI in patients that have an indwelling catheter for >10 days (Sitges-Serra and Linares, *Lancet* 1:668 (1983); Sitges-Serra et al., *Surgery* 97:355-257 (1985); Sitges-Serra et al., *JPEN* 8:668-672 (1984); Linares et al., *J. Clin. Microbiol.* 21:357-360 (1985); Forse et al., *Surgery* 86:507-514 (1979); Moro et al., *Infect. Control Hops. Epidemiol.* 15:253-264 (1994); Llop et al., *Clin. Nutr.* 20:527-534 (2001); Bouza et al., *J. Hosp. Infect.* 54:279-287, (2003); Salzman and Rubin, *Nutrition* 13:15S-17S (1997); Tan et al., *J. Infect. Dis.* 169:1393-1397 (1994)). The hub is often contaminated during manipulation necessary to draw blood samples, administer medication, fluid, or parenteral nutrition. Microorganisms present on or nearby (ostomy, wound, fistula, skin, tracheostomy, blanket/clothing) the external hub surface are transferred to the hub lumen by the patient's, nurse's, or physician's fingers when the catheter hub is handled (De Cicco et al., *Lancet* 2:1258-1260 (1989)). Even 10-20% of piggyback side-ports punctured six times daily become colonized with pathogenic microorganisms (Brismar et al., *Clin. Nutr.* 6:31-36 (1982).

Current hub designs were designed primarily to ensure a tight connection with intravenous tubing, but were not designed specifically to prevent hub and endoluminal catheter microbial colonization. Prevention of hub colonization, and therefore of hub-mediated infections is dependent on the avoidance of contamination during connection/disconnection of tubing, during direct injections, and during blood drawing as well as protection against contamination of the hub while connected to tubing. Experimental evidence has shown that intentional hub surface bacterial contamination leads to 100% internal fluid pathway contamination in an inappropriately disinfected hub and that disinfection of the hub cap will prevent up to 99% of potential contamination of the internal fluid pathway (Ardulno et al., *Am. J. Infect. Control* 26:377-380 (1997)). Needleless systems now in current use may also result in increased infection risk when compared to previous needled systems (Danzig et al., *JAMA* 273:1862-1864 (1995); Kellerman et al., *J. Pediatr.* 129:711-717 (1996)). These systems differ from older needle-containing systems by nature of their hub design.

Therefore, prevention of hub colonization will reduce or prevent the introduction of microorganisms into the catheter lumen. Such prevention may be evoked through careful cleaning and preparation of the catheter prior to use. Often however, such care is less than optimal and, in an emergency situation especially, catheter hubs are not often cleaned appropriately (Stotter et al., *JPEN* 11: 159-162 (1987); Sitges-Serra, *Support Care Cancer* 7:391-395 (1999)). Neither the currently used Luer-lock connector or the rubber membrane "piggyback" system have antimicrobial properties and therefore require strict aseptic manipulation. In addition, proper hub care requires additional training and increases the time required for already constrained health care professionals.

Thus, there exists a need for techniques and devices that can be effective at reducing microbial contamination of a catheter connection. The present invention satisfies this need and provides related advantages as well.

SUMMARY OF INVENTION

The invention provides an injection port cap, comprising a body having a cavity extending from a distal end to a proximate end of the body; a movable frit located within the cavity so as to form a reservoir between the frit and the proximate end of the body; a biasing element arranged to urge the movable frit towards the distal end of the body; and an absorbent element located within the cavity adjacent the distal end of the body.

The invention also provides a catheter cleaning device comprising a body comprising a passageway extending from a proximate opening adjacent a proximate end to a distal end; a penetrable sealing element located adjacent the proximate end within the passageway; an absorbent element located within the passageway between the distal end and the penetrable sealing element; at least one brush located between the penetrable sealing element and the absorbent element; a luer connector located within the passageway between the distal end and the brushes; and a reservoir formed within the passageway between the luer connector and the penetrable sealing element.

The invention additionally provides a catheter cleaning injection port cap, comprising a body comprising a passageway extending from a proximate end to a distal end; the proximate end operable in a closed position and an open position; the body further comprising an actuating member configured to change the proximate end from the closed position to the open position; a plurality of separable absorbent elements located within the passageway adjacent the proximal end; and a fluid impermeable sheath covering at least a portion of an exterior of the body.

DETAILED DESCRIPTION OF THE INVENTION

Figure 1:
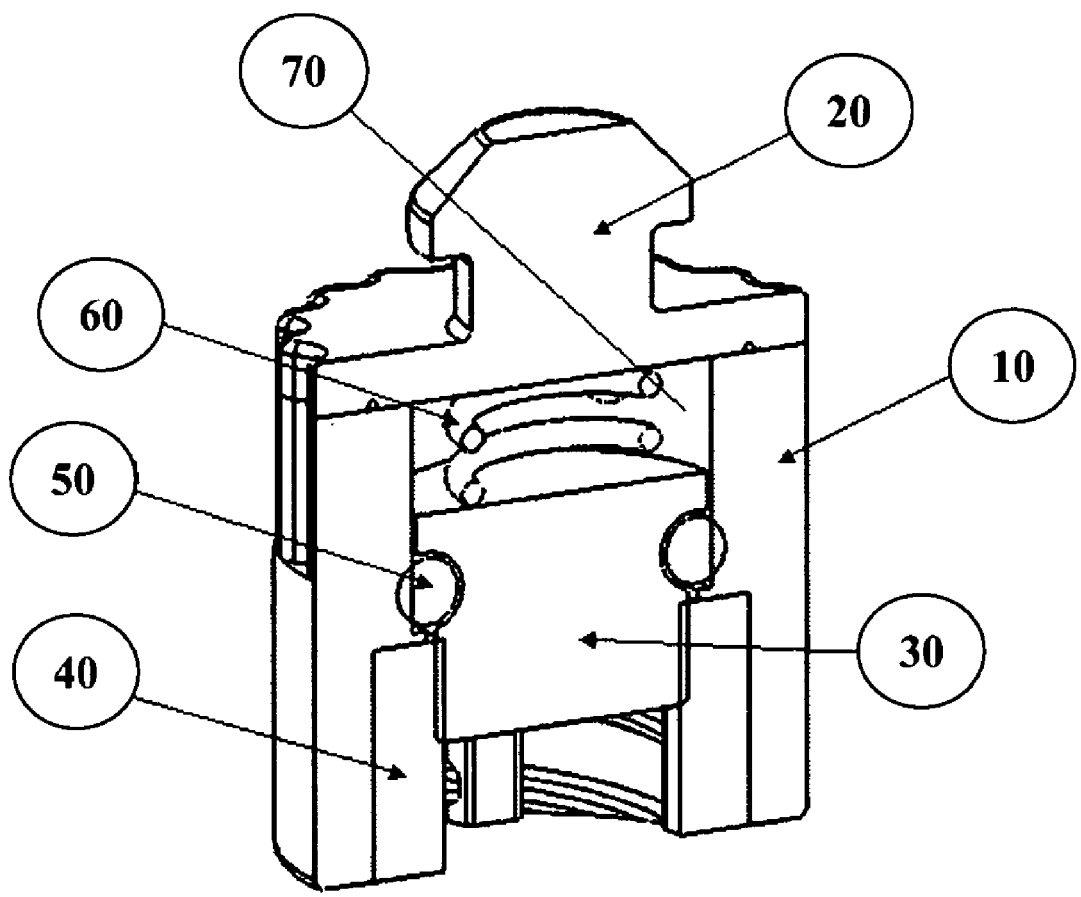
FIG. 1 shows an exemplary catheter cleaning device as a cap design. The cap is made up of two parts, the body 10 and the connector/top 20 as shown in FIG. 1. The other parts include mobile frit 30, open cell wiping foam or sponges 40, O-ring 50, and spring 60. Frit 30 forms a reservoir 70 in the cavity of body 10.

The present invention provides catheter cleaning devices that are effective at reducing microbial contamination of a catheter port entry. The catheter cleaning devices of the invention reduce the potential for introducing infection into a patient via a catheter port entry. The catheter cleaning devices of the invention reduce microbial contamination at a catheter port entry by continually cleaning the port entrance by bathing it in an antimicrobial solution. The catheter cleaning devices also incorporate scrubbing surfaces that function to scrub the catheter connection as well as apply antimicrobial solution. Thus, the catheter port is bathed in antimicrobial solution, keeping the parts aseptic and clean.

As disclosed herein, a device has been developed that is designed to be used with a needleless intravenous system that will ensure the catheter hub is always disinfected regardless of the technique used to connect the catheter or lack of catheter care. This device also decreases the incidence of hub contamination, catheter lumen microbial colonization, and therefore, the risk for CRBI. This antimicrobial barrier effectively prevents endoluminal catheter contamination. A previous hub model that incorporated a chamber of 3% iodinated alcohol into which a needle would pass prior to insertion into the catheter was effective in the prevention of endoluminal catheter microbial colonization both in vitro and in vivo (Segura et al., *J. Clin. Microbiol.* 27:2656-2659 (1989); Segura et al., *J. Clin. Microbiol.* 28:2551-2554 (1990); Segura et al., *Ann. Surg.* 223:363-369 1996)).

Based on the results of a meta-analysis of eight studies and several more recent investigations, results have shown that skin preparation with chlorhexidine (0.5% or 10% chlorhexidine gluconate alcohol solution or 0.5% or 2% chlorhexidine gluconate aqueous solution) is more effective than 10% povidone-iodine for prevention of bacterial colonization and CRBI (Chaiyakunapruk et al., *Ann. Intern. Med.* 136:792-801 (2002); Maki et al., *Crit. Care Med.* 28:A42 (2000); Garland et al., *Pediatrics* 107:1431-1436 (2001); Casey et al., *J. Hosp. Infect.* 54:288-293 (2003)), current standard of care now includes disinfection of the catheter hub with chlorhexidine (Northwestern Memorial Hospital (NMH) nursing protocol; Inoue et al., *JPEN* 16:581-585 (1992); Bouza et al., *J. Hosp. Infect.* 54:279-287 (2003)).

The catheter cleaning devices of the invention are intended to reduce colonization of the bacteria that reside on the surface of the needleless injection port entry area. When the mating luer fitting is inserted into the port, a person with a central venous catheter (CVC) has to clean the entry port up to 42 times per week. Every time this is done there is a slight chance that bacteria will be introduced into the patients venous system. Improper cleaning of the port entry area allows the bacteria to enter the port. The present invention reduces the bacteria available for accidental insertion by continually bathing the needleless port in an antimicrobial solution such as isopropyl alcohol (IPA) and chlorhexidine (CHG) mix. This solution has been shown to be very effective against bacteria and other microorganisms.

Currently hospitals generally use a procedure to simply wipe the area of the port with three Chloraprep™ one-step wipes. These wipes are not easy to use on small objects and it is very subjective as to who and how the ports are cleaned in determining how well the bacteria count is reduced. Improper, hurried, or sloppy cleaning procedures will lead to a greater chance of bacterial ingress.

As used herein, a "bloodstream infection" refers to a blood culture that is positive for microbes such as bacterial or fungal microorganisms.

As used herein, a "catheter-related bloodstream infection" or "CRBI" refers to the occurrence of a bloodstream infection in a patient with a central venous catheter (CVC) in whom another source of infection is not wound, urine, respiratory, or intra-abdominal in origin.

As used herein, "catheter endoluminal colonization" refers to the presence of viable microorganisms such as bacteria or yeast, which can be grown in culture, on the inside walls of a catheter in the absence of positive blood cultures or any septic focus.

As used herein, a "catheter hub" refers to the junction between the intravenous catheter and intravenous tubing or other connection device.

In one embodiment, the invention provides a catheter cleaning device that is a cap design. The cap design for a catheter cleaning device is screwed on to a standard luer fitting of a needleless injection port.

An exemplary catheter cleaning device that is a cap design contains a body 10 and a connector/top 20, as shown in FIG. 1. The body 10 and connector/top 20 can be ultrasonically welded or adhesively joined together, for example, during final assembly after all the other parts are installed. The other parts of a catheter cleaning device that is a cap design include mobile frit 30 for slow transfer of cleaning solution, open cell scrubbing surface such as a wiping foam or sponges 40 to clean the port threads, O-ring 50 to seal the solution into its reservoir and a spring 60 to push frit 30 distally when the device is not installed onto a port. Reservoir 70 is for an antimicrobial solution such as IPA and CHG antimicrobial cleaning solution. The device cleans the CVC needleless port by screwing onto the luer fitting and pushing the mobile frit 30 up into reservoir 70. The increased pressure in the reservoir forces the solution through the frit 30 and into the foam 40, which in turn bathes the port opening in the antimicrobial solution and has a scrubbing action on the luer top, injection port piston, and threads. When a male luer is to be attached to a catheter, this device is removed, but can be tethered to the CVC port by an optional strap that runs between connector/top 20 and the port. The spring 60, during removal of the device, pushes the frit 30 out, creating a slight vacuum, which draws the solution back into reservoir 70. This vacuum limits the amount of solution evaporation when the cap is not installed onto a luer fitting. When the cap is then reattached to the luer, the frit 30 is again forced into reservoir 70 and the solution is forced into frit 30 and foam 40, re-bathing the needleless port in antimicrobial solution. As the frit 30 is pushed further into reservoir 70, the device can optionally contain a window to observe a visual indicator, in which O-ring 50, which can be colored to facilitate visualization, can be visualized through a clear section on the side of body 10, indicating the antimicrobial solution is low in volume and a new cap should be installed. The frit 30 and scrubbing foam 40 and the positive pressure on the antimicrobial cleaning solution continually bathe the port entrance. The negative pressure from the reservoir limits evaporation of the cleaning solution when not attached to the catheter port.

In one embodiment, the invention provides a catheter cleaning device, comprising a body having a cavity; a movable frit disposed in the cavity, whereby the frit is positioned to form a reservoir in the cavity; a spring disposed in the reservoir; an o-ring disposed between the frit and the wall of the cavity; and a scrubbing foam disposed in the cavity proximal to the frit and distal to the reservoir. The catheter cleaning device can further comprise a window positioned to indicate the position of the frit in the cavity. The catheter cleaning device can further comprise an antimicrobial solution dispersed in the reservoir.

In another embodiment, the invention provides an injection port cap, comprising a body having a cavity extending from a distal end to a proximate end of the body; a movable frit located within the cavity so as to form a reservoir between the frit and the proximate end of the body; a biasing element arranged to urge the movable frit towards the distal end of the body; and an absorbent element located within the cavity adjacent the distal end of the body. In such an injection port cap, the frit can be comprised of a porous material.

In an injection port cap of the invention, the biasing element can comprise a spring, for example, a helical spring, which can be located within the reservoir. An injection port cap of the invention can contain an absorbent element comprising a sponge.

In an embodiment of an injection port cap of the invention, the frit can be configured to provide a fluid pathway between the reservoir and the absorbent element. The liquid in the reservoir of an injection port cap can be forced through the frit to the absorbent element when the frit is moved against the biasing element towards the proximate end of the body. Generally, the cavity of the injection port cap of the invention has a substantially cylindrical shape.

In an injection port cap of the invention, the absorbent element can be located along at least a portion of a circumference of the cavity adjacent the distal end of the body. The body of an injection port cap can further comprise a window positioned to indicate a position of the frit or to indicate the level of liquid in the reservoir.

In an injection port cap, the cavity can comprise a closed end at the proximate end of the body and an opening at the distal end of the body. In such an injection port cap, the reservoir can be located between a top surface of the frit and the closed end of the cavity. Generally, the opening of the cavity of an injection port cap is sized to accommodate a catheter. In a particular embodiment, the opening of the cavity can further comprise screw threads adjacent the distal end of the body, for example, where the screw thread are configured to accommodate a luer fitting of a needleless injection port.

In an injection port cap of the invention, the cap can further comprise a sealing member located between a side surface of the frit and an inner surface of the cavity. For example, the sealing member can comprise an elastomer o-ring located around the side surface of the frit. An injection port cap of the invention can further comprise an antimicrobial solution located within the reservoir.

In another embodiment, the invention provides a catheter cleaning device having a penetration design. The penetration design for a catheter cleaning device replaces the current needleless injection port with an all in one design. This device has the needleless injection port system included in the design.

Figure 2:
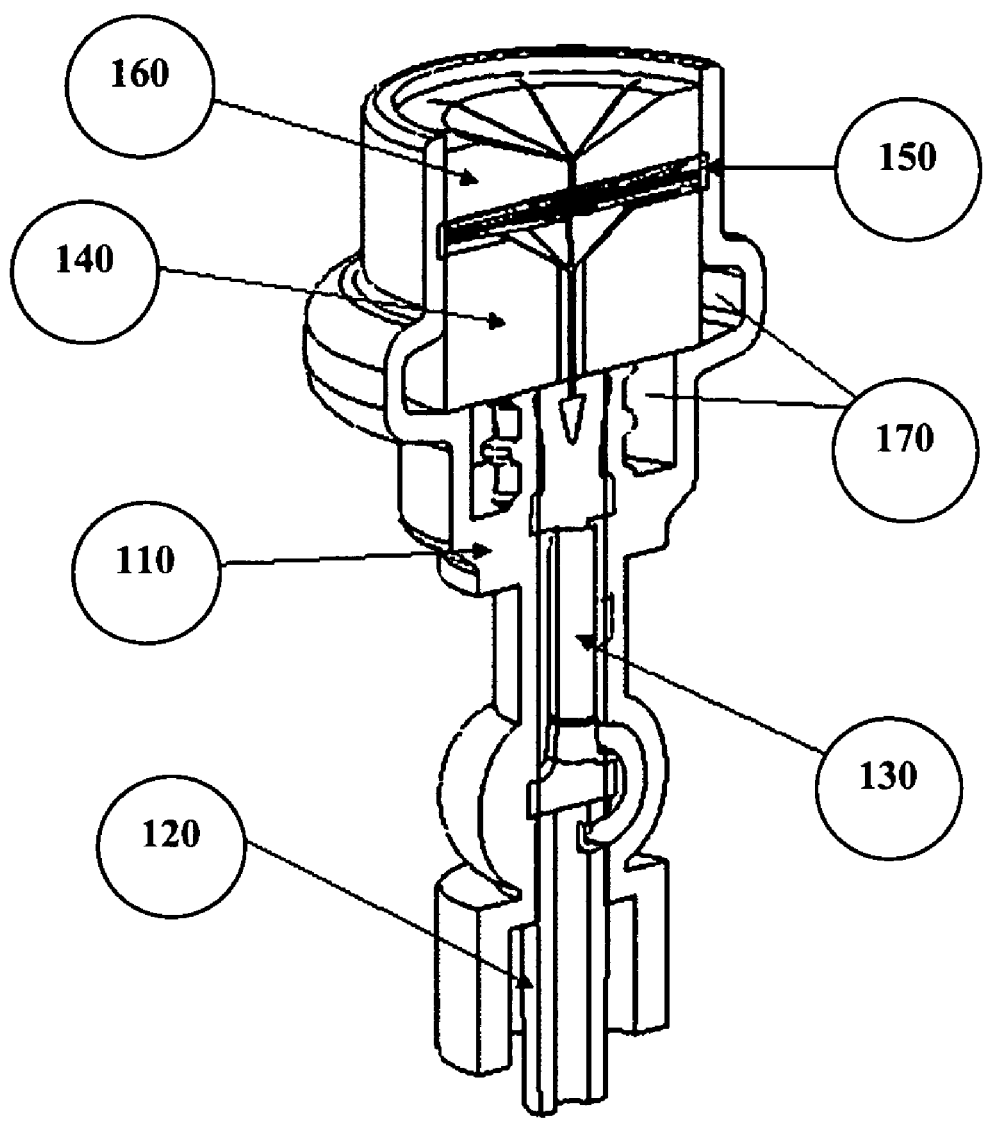
FIG. 2 shows an exemplary catheter cleaning device as a penetration design. The parts that make up the port of the penetration design include device body 110 with luer threads included for attachment to the central venous catheter (CVC) and the feeding tube or male luer. The other parts include the bottom plug 120 that is in the male luer to the CVC, piston 130, scrubbing memory open cell foam 140, scrubbing brushes 150 and sealing foam 160.

An exemplary catheter cleaning device having a penetration design has parts that make up the port, which include device body 110 with luer threads included for attachment to the central venous catheter (CVC) and the feeding tube or male luer (see FIG. 2). The other parts include bottom plug 120 that is in the male luer to the CVC and piston 130 that is compressed to allow fluid flow. The new parts of the device are the scrubbing surface/memory open cell foam 140, scrubbing brushes 150 to assist cleaning of the incoming luer and displacement of scrubbing surface 140, and sealing foam 160 to retain solution and protect against evaporation. Sealing foam 160 should remain moist and antimicrobial. Reservoir 170 contains antimicrobial solution.

The catheter cleaning device having a penetration design replaces the standard needleless port of the CVC so that the entrance to the catheter by the top of the piston 130 is continually bathed in antimicrobial solution such as IPA/CHG solution. When the male luer connector is needed, it is pushed through the sealing foam 160, brushes 150, and scrubbing foam 140 and screwed onto the female luer fitting. The scrubbing foam 140, sealing foam 160 and brushes 150 are pushed to the radial sidewalls, and the antimicrobial solution is displaced into the reservoir 170. When the male luer is removed, the scrubbing foam 140 resumes its position and covers the port opening and bathes it in an antimicrobial solution such as IPA/CHG solution. The brushes 150 and sealing foam 160 also resume their original positions to seal out the microbes. The antimicrobial solution re-penetrates brushes 150, scrubbing foam 140, and sealing foam 160, cleaning them and making them antimicrobial surfaces. The scrubbing foam 140, sealing foam 160, and brushes 150 of the device protect the catheter entrance from microbial ingress.

In another embodiment, the invention provides a catheter cleaning device, comprising a body having a cavity; a plug disposed in the cavity; a piston positioned proximal to the plug in the cavity; a scrubbing foam proximal to the piston; brushes proximal to the scrubbing foam; a seal proximal to the brushes; and a reservoir in the cavity adjacent to the scrubbing foam, whereby insertion of a male luer allows penetration through the scrubbing foam, brushes and seal and displacement of fluid into the reservoir. The catheter cleaning device can further comprise an antimicrobial solution dispersed in the scrubbing foam and brushes.

In yet another embodiment, the invention provides a catheter cleaning device comprising a body comprising a passageway extending from a proximate opening adjacent a proximate end to a distal end; a penetrable sealing element located adjacent the proximate end within the passageway; an absorbent element located within the passageway between the distal end and the penetrable sealing element; at least one brush located between the penetrable sealing element and the absorbent element; a luer connector located within the passageway between the distal end and the brushes; and a reservoir formed within the passageway between the luer connector and the penetrable sealing element. In such a catheter cleaning device, the luer connector can be a female luer connector. The penetrable sealing element of a catheter cleaning device can comprise absorbent foam.

In a catheter cleaning device of the invention, the penetrable sealing device can be configured to operate in a first position when a luer fitting is inserted within the proximate opening and in a second position when no luer fitting is inserted within the proximate opening. For example, the penetrable sealing element can compress radially when operating in the first position. The penetrable sealing device can be configured to reduce evaporation of a fluid within the passageway operating in the second position.

In a catheter cleaning device of the invention, the absorbent element can include a central opening having a major axis substantially in-line with a major axis of the passageway. An inner surface of the absorbent element along its central opening can be configured to contact a luer fitting positioned adjacent the luer connector. In another embodiment, a bottom portion of the absorbent element can be located adjacent a top portion of the luer connector.

The absorbent element of a catheter cleaning device of the invention can be at least partially impregnated with antimicrobial solution. The absorbent element of a catheter cleaning device can be configured to radially compress when a luer fitting is attached to the luer connector such that a portion of the antimicrobial solution travels from the absorbent element to the reservoir. The portion of the antimicrobial solution in the reservoir can be located adjacent to an interface between the luer fitting and the luer connector.

A catheter cleaning device can further comprise a piston located within the passageway and extending from the luer connector through the distal end of the body. In a catheter cleaning device, the penetrable sealing element can comprise foam. The absorbent element can comprise open cell foam.

In yet another embodiment, the invention provides a catheter cleaning device that has a pop open design. The pop open design for a catheter cleaning device bonds the newly designed cap to a currently produced luer activated needleless injection port/connector. This new combination unit is used instead of the current plain injection port on the CVC catheters.

Figure 3:
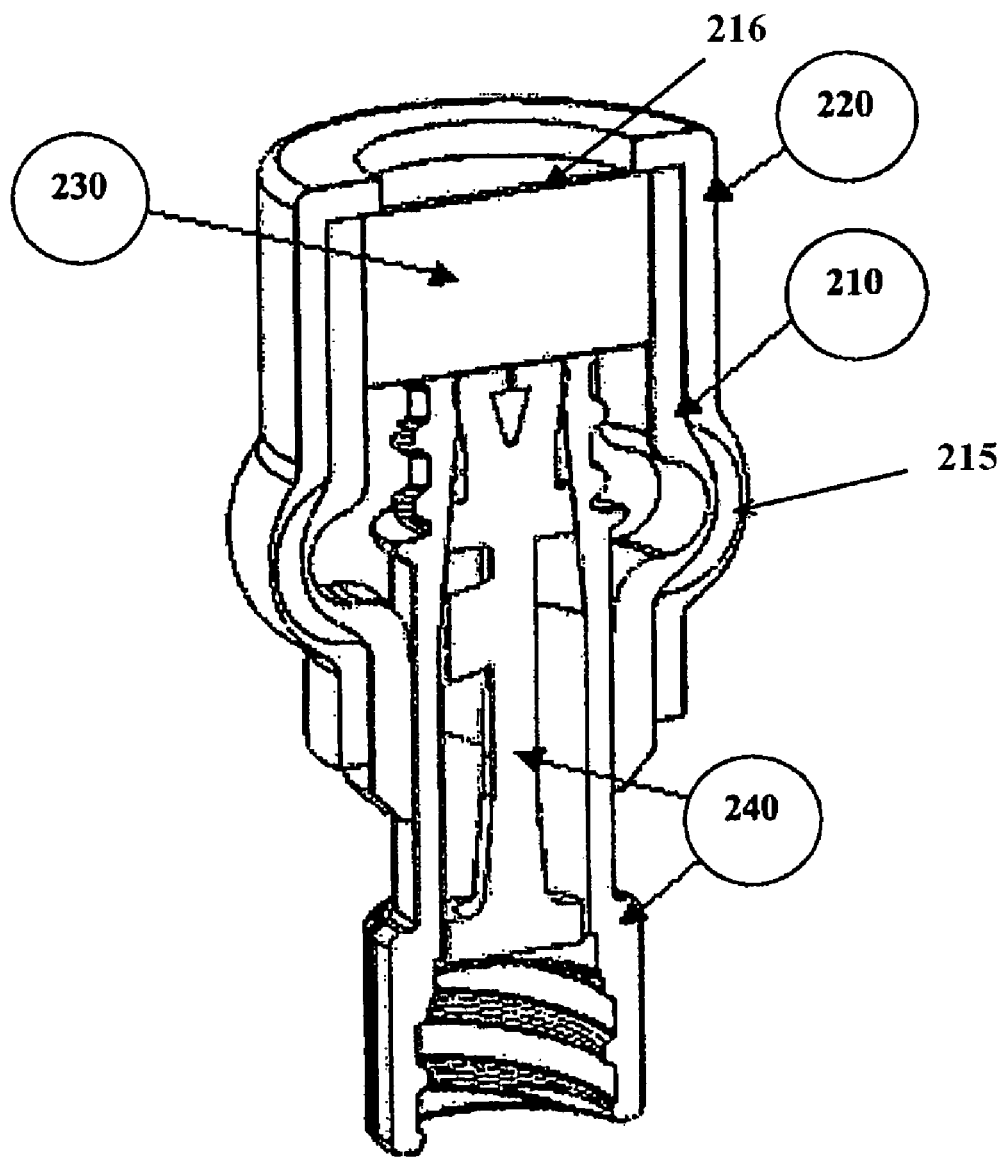
FIG. 3 shows an exemplary catheter cleaning device as a pop open design. The pop open cap design is made up of three parts, the device body 210, the fluid sheath 220, and scrubbing/bathing foam 230. Also shown is a separate luer activated needleless valve/port/connector 240. The position depicted is the "closed" position.
Figure 4:
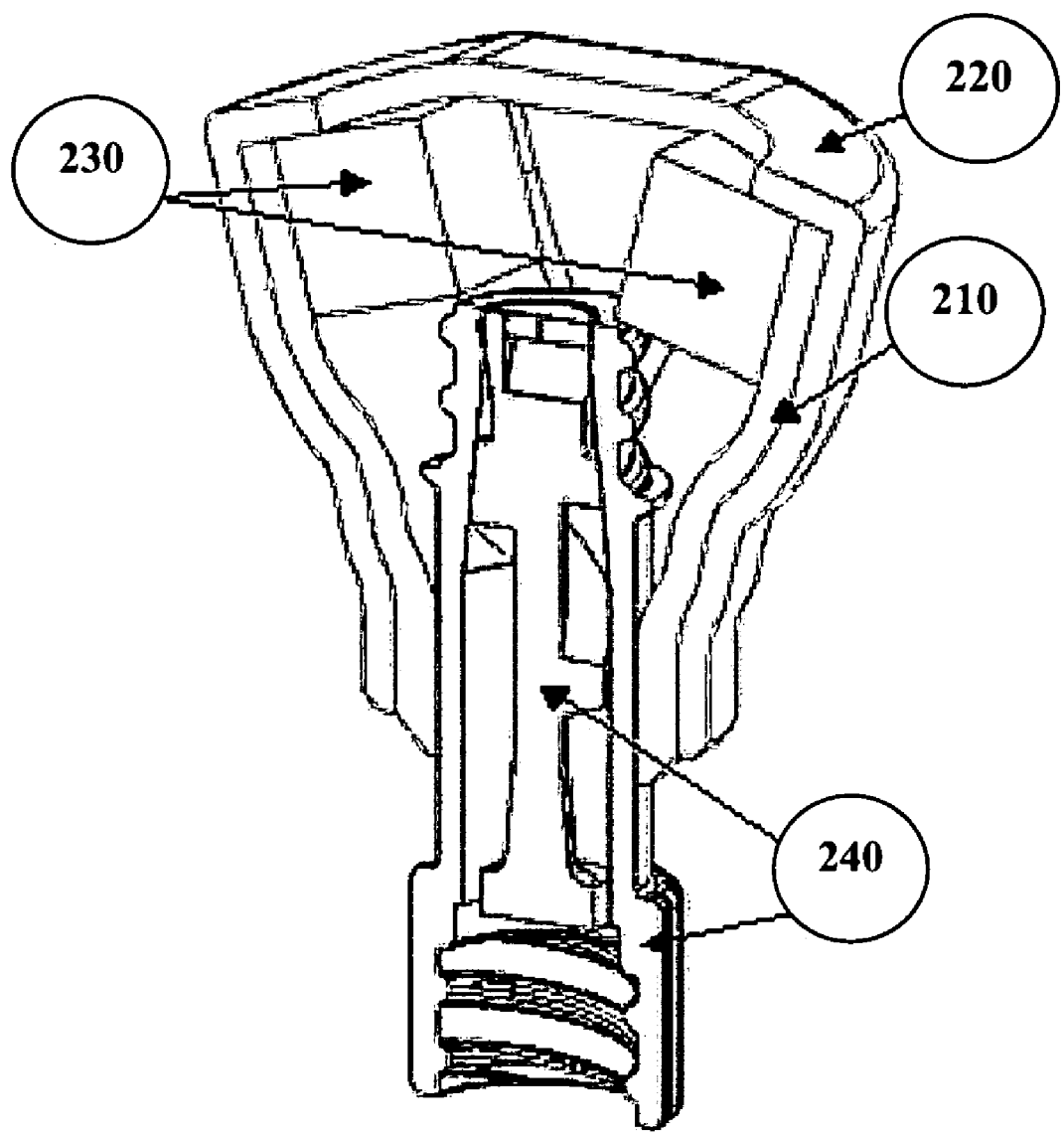
FIG. 4 shows the catheter cleaning device shown in FIG. 3 depicted in the "open" position.

An exemplary catheter cleaning device having a pop open cap design has the device body 210, the fluid sheath 220, and scrubbing surface/bathing foam 230, as shown in FIG. 3, depicted in the "closed" position. The body device 210 contains bumped sides that can be compressed so that the device body 210 is in the "open" position (depicted in FIG. 4). The only other part in this design is the commercially available luer activated needleless valve/port/connector 240. The bathing foam 230 has a membrane to limit evaporation of the cleaning solution that permeates the foam. Two pieces of bathing foam 230, approximate half cylinders, are bonded to the device body 210 with the membrane side facing out or externally. This assembly is then bonded and sealed onto the commercially available needleless valve such that the foam parts are in contact with the needleless valve opening. This proximity will allow scrubbing foam 230 to scrub the valve opening on actuation and closure of the cap/device. Also, the constant contact with the valve opening will allow continual bathing with the antimicrobial solution such as IPA and CHG solution. The next step is bonding the fluid sheath 220 to the external surface of the device body 210 along the base to prevent leakage of antimicrobial solution and along the spines on the body to ensure proper placement of the sheath. The fluid sheath 220 and device body 210 can be ultrasonically welded or adhesively joined together. This sheath acts as a second skin that helps contain the antimicrobial solution, closes the cap end on luer port removal, and blocks debris from entering into the part when the luer port is installed. Finally the antimicrobial solution is added to the scrubbing foam 230 internal to the membrane.

This final assembly is then used instead of a standard needleless port of the CVC so that the entrance to the catheter by the top of the needless valve/port/connector 240 is continually bathed in antimicrobial solution. When a luer needs to be connected to the port, the device is squeezed on the bumped sides, which splits open the bathing foam scrubbers 230 and reveals the female luer fitting in a cleaned condition (see FIG. 4). The male luer is inserted and the sides are released, enveloping the connection in a protected environment. Upon completion of accessing the needleless valve, the male luer is unscrewed and removed, and the foam is compressed together over the needless valve opening, re-bathing it in antimicrobial solution until the next access is needed. This closed position also protects the valve opening from direct contamination from external sources. The foam 230 protects the entrance from microbial ingress. The device body is a firmer plastic and, when the sides of the device are squeezed, the plastic deforms, forcing the two halves of the device open and allowing access to the luer valve. The fluid sheath is made of a very elastic material that stretches open from the force imparted on it from the plastic device body as it deforms.

Figure 5:
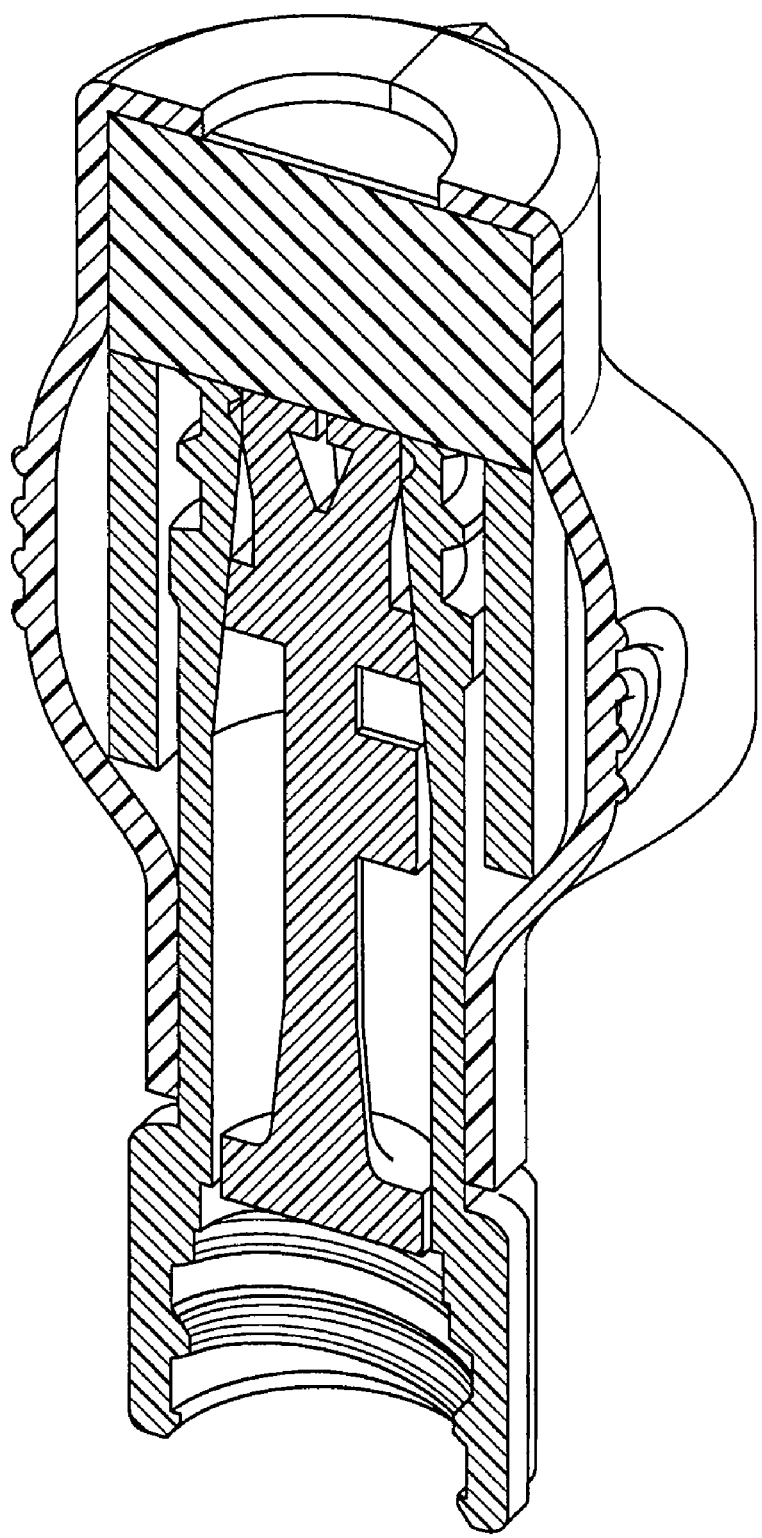
FIG. 5 shows an exemplary catheter cleaning device in section view.
Figure 6:
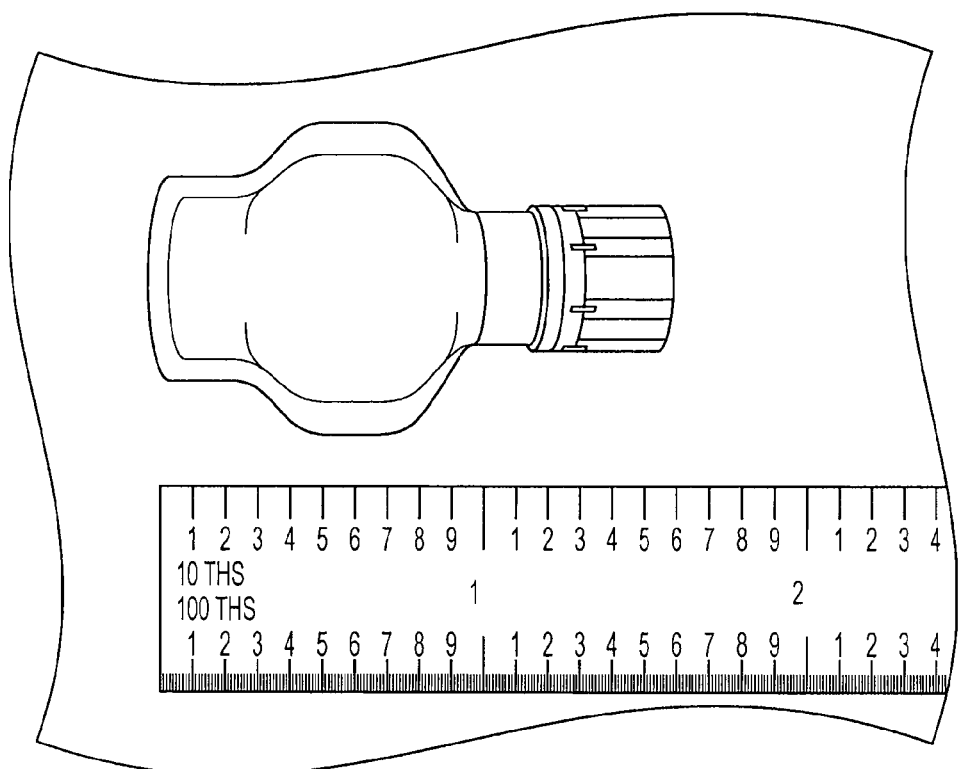
FIG. 6 shows a side view of an exemplary catheter cleaning device.
Figure 7:
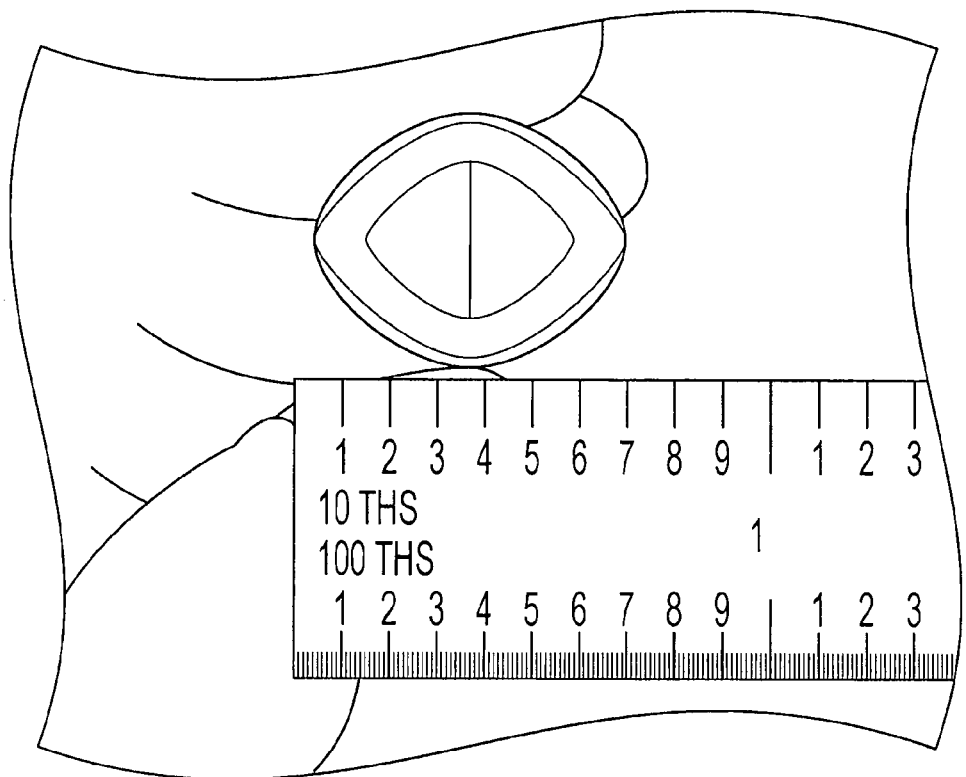
FIG. 7 shows a top view of an exemplary catheter cleaning device.

An exemplary catheter cleaning device is depicted in FIG. 5. Such an exemplary catheter cleaning device is also referred to herein as a "cap" or "AB cap." An exemplary catheter cleaning device was produced, as shown in FIGS. 6-12 and described in Example II.

In yet another embodiment, the invention provides a catheter cleaning device, comprising a body having a cavity and a compressible position; a scrubbing foam disposed in the cavity; wherein the scrubbing foam has a fluid impermeable member 216 that faces outward from the cavity, and a needleless port disposed in the cavity. Such a catheter cleaning device can further comprise an antimicrobial solution dispersed in the scrubbing foam.

In still another embodiment, the invention provides a catheter cleaning injection port cap, comprising a body comprising a passageway extending from a proximate end to a distal end; the proximate end operable in a closed position and an open position; the body further comprising an actuating member 215 configured to change the proximate end from the closed position to the open position; a plurality of separable absorbent elements located within the passageway adjacent the proximal end; and a fluid impermeable sheath covering at least a portion of an exterior of the body. In such a catheter cleaning injection port cap, the absorbent elements can be impregnated with an antimicrobial solution. The absorbent elements can form a substantially closed surface when the proximate end is operated in the closed position. The absorbent elements can be spatially separated from one another when the proximate end is operated in the open position.

In a catheter cleaning injection port cap of the invention, the proximate end can be configured to accommodate a luer fitting when operated in the open position. One or more of the absorbent elements can be configured to contact an exterior of a luer fitting being inserted in the proximate end. In a catheter cleaning injection port cap of the invention, the plurality of separable absorbent elements can include two substantially half cylindrical sponges, wherein the sponges are adjacent one another when the proximate end is operated in the closed position and separate from one another when the proximate end is operated in the open position.

The body of a catheter cleaning injection port cap of the invention can be constructed of a deformable material. The actuating member of a catheter cleaning injection port cap of the invention can comprise at least one compressible portion protruding radially outward from a major axis of the passageway. For example, when the at least one compressible portion is compressed, the proximate end is in the open position; and when the at least one compressible portion is uncompressed, the proximate end is in the closed position. The distal end of a catheter cleaning injection port cap can be bonded to a needleless valve. For example, a bottom surface of the absorbent element is adjacent an opening of the needleless valve when the distal end is bonded to the needleless valve.

The catheter cleaning devices of the invention can include antimicrobial solutions to clean and sanitize catheter port entries. In one embodiment, the antimicrobial solution is a mixture of isopropyl alcohol and chlorhexidine or aqueous chlorhexidine. For example, the antimicrobial solution can contain about 0.05% to about 10% chlorhexidine gluconate (CHG), particularly about 0.05% to about 4%, for example, about 0.1%, about 0.2%, about 0.5%, about 1%, about 2%, about 3%, about 4%, about 5%, about 6%, about 7%, about 8%, about 9% or about 10%. A particularly useful antimicrobial solution is about 2% chlorhexidine in 70% isopropyl alcohol. Other suitable alcohols can also be used or mixtures of alcohols. The alcohol generally ranges from about 50% to about 80%, in particular about 70% or 75% alcohol. Alternatively, an aqueous solution of chlorhexidine gluconate, in the range of about 0.5% to about 2% of CHG, can be used as an antimicrobial solution. Other suitable antimicrobial solutions include iodine and its derivatives, for example, iodinated alcohol, for example, 3% iodinated alcohol, and povidone-iodine, for example, a 10% solution, or other suitable concentrations having antimicrobial activity. Other suitable antimicrobial solutions include silver sulfadiazine or other antiseptics. It is understood that mixtures of various antimicrobial agents can also be used. These and other antimicrobial solutions are well known to those skilled in the art (Segura et al., *J. Clin. Microbiol.* 27:2656-2659 (1989); Segura et al., *J. Clin. Microbiol.* 28:2551-2554 (1990); Segura et al., *Ann. Surg.* 223:363-369 1996); (Chaiyakunapruk et al., *Ann. Intern. Med.* 136:792-801 (2002); Maki et al., *Crit. Care Med.* 28:A42 (2000); Garland et al., *Pediatrics* 107:1431-1436 (2001); Casey et al., *J. Hosp. Infect.* 54:288-293 (2003)), Inoue et al., *JPEN* 16:581-585 (1992); Bouza et al., *J. Hosp. Infect.* 54:279-287 (2003)).

While the catheter cleaning devices of the invention described above and depicted in FIGS. 1-4 show specific embodiments, it is understood by those skilled in the art that modifications of the devices can be made so long as the catheter port connections are bathed in an antimicrobial solution and reduce microbial contamination of a catheter port entry. One skilled in the art can readily determine suitable modifications of the catheter cleaning devices of the invention.

For any of the catheter cleaning devices of the invention, various modifications can be made to facilitate replenishment or dispersal of antimicrobial solution to appropriate places within the device. For example, a valve system can be added to introduce fresh antimicrobial solution to the device in order to penetrate or cover the frits, foam, or surfaces of the devices. Optionally, the valve can have an aperture or iris, such as found in a camera, to seal off the valve top and clean it on opening. In addition, a pressure piston can be used to encourage fluid transfer to facilitate dispersal of the antimicrobial solution to needed locations within the device. In addition, a screw mechanism or detent system can be included to create pressure to facilitate movement of the antimicrobial solution. This can serve to increase fluid capacity of the catheter cleaning devices of the invention, particularly in the cap design device. Vents can also be included on the catheter cleaning devices of the invention to help transfer fluid from a reservoir to materials to be contacted with the antimicrobial solution such as the foams that wipe the threads for the cap design or the foam and brushes of the penetration design. In addition, a catheter cleaning device can include an additional reservoir of antimicrobial solution that can be used to replenish the solution available for cleaning catheter connections. For example, a reservoir can contain a seal or valve that allows infusion of antimicrobial solution into the device, for example, by holding the device in a particular position, or the solution can be infused by squeezing a compressible reservoir. Such a reservoir can also be combined with the modifications described above to facilitate replenishment or dispersal of antimicrobial solution in the catheter cleaning device.

Additional modifications of a catheter cleaning device of the invention can include foam formed around a needleless port to prevent additional loss of fluid. For example, the foam in the device can have finger like projections that reach down to the end of the threads of the luer, closer to the cylindrical body of the luer body. The fingers can be lightly compressed on an area to catch any loose fluid in the device and help soak it into the main body of the foam. This could greatly help fluid loss if the device is activated when upside down. In addition, the scrubbing surface made of foam or sponge can be designed to plunge deeper into the device to help wick up antimicrobial solution. In addition, coloration can be incorporated into the scrubbing surface or foam, or other components of the device, to help target the connecting luer into the appropriate position in the device. Furthermore, the foam can incorporate a color change that reflects evaporation of the antimicrobial solution, for example, evaporation of alcohol, which can be used to conveniently indicate a need to use a new device. In addition, modifications can be incorporated into specific devices suitable for the particular device.

For a catheter cleaning device having a cap design, the device can include a threaded frit that can be used to limit over tightening and over pressurization of the reservoir. Furthermore, the scrubbing surface/foam of the cap design can be omitted so as not to clean the threads of the luer fittings. In such a case, a seal is provided in place of the foam to retain the microbial solution in the device. Instead, the device provides antimicrobial solution to bathe the catheter connections without the scrubbing action of the foam.

For a catheter cleaning device having a penetration design, a plastic cap can be included to cover the opening to prevent evaporation and ingress of microbes. A catheter cleaning device having a penetration design can also include foam or sponges placed into the reservoirs to insure wicking action and full saturation of scrubbing foams. In addition, the scrubbing foams can optionally be omitted, relying on the brushes to seal and clean the port entrance.

For a catheter cleaning device having a pop open design, colored targets on the sides of the pop open device can be used to indicate where to push to activate/open the cap.

The invention additionally provides a catheter cleaning device that is a wiping cap that is suitable to clean existing needleless catheter components. Such a wiping cap is a sealed cap with foam inserts approximating the size of the luer systems. As with the catheter cleaning devices of the invention, the foam can be saturated with antimicrobial solution to clean the ends of needleless port. This design allows good coverage of the port entry area with antimicrobial solution. The device can be disposed of after each use, if desired. Such a device conveniently substitutes for the physical wiping of catheter ports as currently practiced by health care professionals and eliminates variability between health care professionals using current practice. In such a design, the open end can be covered by a cap to prevent evaporation of antimicrobial solution prior to use.

The invention also provides a catheter cleaning device, comprising a body having a cavity, the body having a closed end and an open end; a scrubbing foam disposed in the cavity, and an antimicrobial solution dispersed through the scrubbing foam.

The invention further provides a method of adapting a luer activated needleless valve by bonding a catheter cleaning injection port cap over an opening of the luer activated needleless valve. In a particular embodiment of the method, the catheter cleaning injection cap can comprises a body comprising a passageway extending from a proximate end to a distal end; the proximate end operable in a closed position and an open position; the body further comprising an actuating member configured to change the proximate end from the closed position to the open position; a plurality of separable absorbable elements located within the passageway adjacent the proximal end; and a fluid impermeable sheath covering at least a portion of an exterior of the body.

The invention additionally provides a method of inhibiting microbial infection in an individual by using a catheter cleaning device of the invention. The method is useful for inhibiting infection of an individual with non-viral, non-protozoal, non-mold human infectious organisms. Thus, the method is useful for inhibiting or preventing infection at a catheter site by decreasing the likelihood of infection with Gram positive, Gram negative or non-mold fungi such as yeast.

It is understood that modifications which do not substantially affect the activity the various embodiments of this invention are also provided within the definition of the invention provided herein. Accordingly, the following examples are intended to illustrate but not limit the present invention.

Example I

Testing of Catheter Cleaning Device for Reducing Microbial Contamination of a Catheter Port Entry This example describes testing the effectiveness of the catheter cleaning devices.

The outer portion a catheter cap of a CVC needleless port is swabbed with various amounts of microbial cultures. Particularly, representative microorganisms are selected from Gram positive, Gram negative and fungi. The microbial cultures tested are *Staphylococcus aureus, Klebsiella pneumonia, Escherichia coli, Candida* species such as *Candida albicans*. Other microorganisms can similarly be tested, for example, *Staphylococcus epidermidis, Klebsiella planticola, Pseudomonas aeruginosa*, and the like. These and other human infectious microorganisms can be similarly tested.

The testing involves swapping the outer portion of a catheter cap (the portion through which the male luer will pass) with 2000 cfu's (colony forming units) of bacteria or fungi. Other amounts of microbial cultures can also be tested. Sterile tubing is connected to the device, using the male luer to the female portion contained within the device, for example with a catheter cleaning device having a penetration design. Saline is then infused and the effluent is plated and cultured to detect and quantify microbial growth.

Similar experiments are conducted with other devices of the invention by swabbing with bacteria or fungi the outer portion of the catheter connection to be used with a particular device. The catheter is then connected, and saline is infused and collected. The effluent is cultured to detect and quantify microbial growth.

Example II

Generation of a Catheter Cleaning Device

This example describes the generation of an exemplary catheter cleaning device. Such a device is also referred to as a "cap" or "AB cap."

A catheter cleaning device or cap was designed to keep needleless luer valves clean by encapsulating them in a cleaning solution. A cap was attached to a standard production needleless luer valve that is able to be squeezed open for attachment of a male luer lock. The AB cap has three main components, the inner shell (white piece; see top view in FIG. 7), the outer membrane sheath (foggy clear exterior covering; see top view in FIG. 7), and foam brushes (yellow interior; see top view in FIG. 7).

The AB cap was glued over a standard production needless luer valve, such as an InVision-Plus® needless luer valve (RyMed Technologies, Inc.; Franklin Tenn.). Any type of needless luer valve suitable for a catheter cleaning device can be used, including any other manufacturers of needless luer valves. The foam brushes abut up to the entrance of the needless luer (see FIG. 5).

Figure 8:
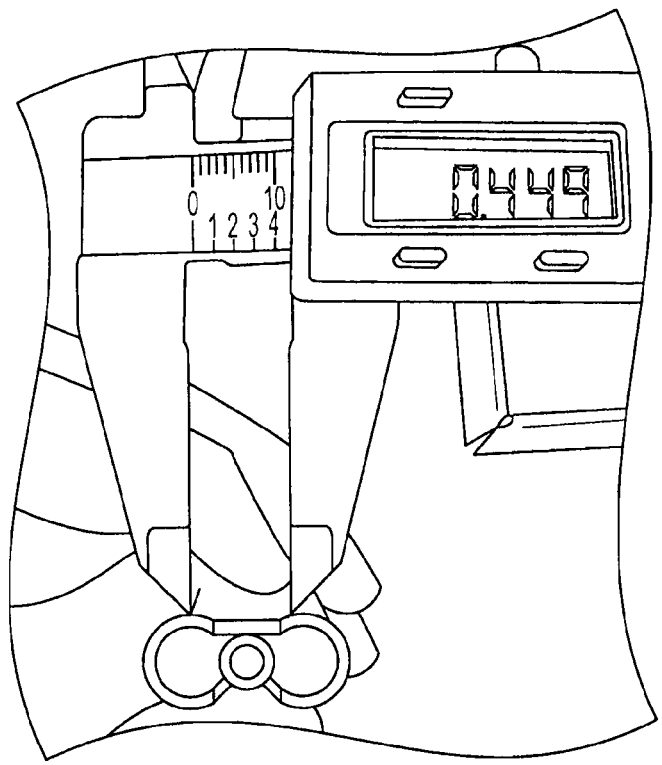
FIG. 8 shows an exemplary catheter cleaning device in the "open" position, with a measurement of the open position shown.
Figure 9:
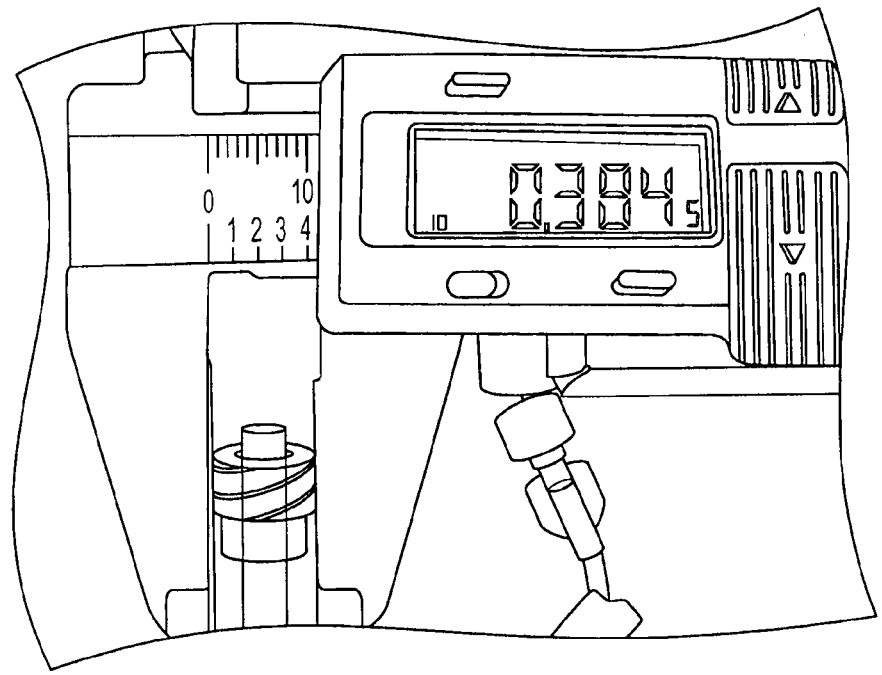
FIG. 9 shows an exemplary male luer with measurement of its diameter.
Figure 10:
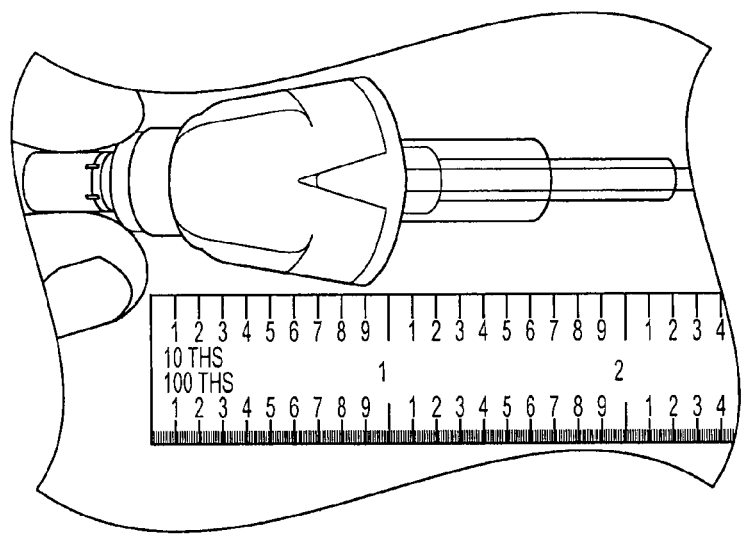
FIG. 10 shows a male luer entering an exemplary catheter cleaning device.
Figure 11:
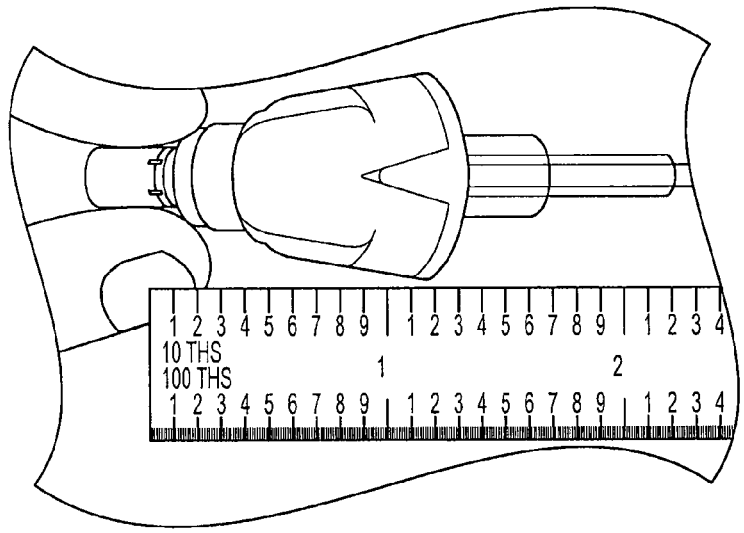
FIG. 11 shows a male luer locked into an exemplary catheter cleaning device.
Figure 12:
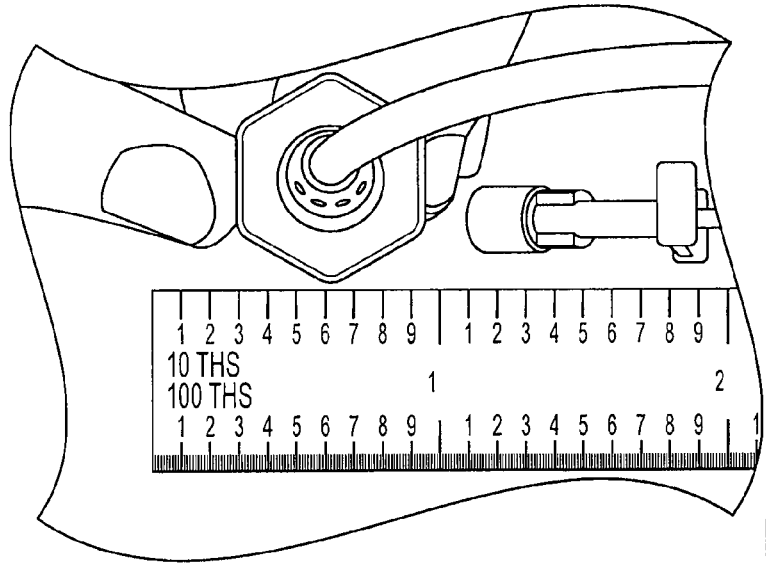
FIG. 12 shows a top view of a male luer inserted and locked into an exemplary catheter cleaning device.

Based on the measurements of a typical threaded male luer lock and the opened AB cap, the luer easily passes into the device and reaches the plunger of the needleless luer valve (see FIGS. 6-12). Furthermore, FIG. 8 shows that, with the luer open, the green plunger of the needleless injection valve can easily be seen while the foam brushes of the AB cap, positioned laterally, are not in a position to interfere with the attachment of the male luer. FIGS. 10, 11 and 12 detail the male luer attachment to the needleless injection port and demonstrate that, once the AB cap is released, it envelopes the male luer until the process is reversed by removing the male luer.

Throughout this application various publications have been referenced. The disclosures of these publications in their entireties are hereby incorporated by reference in this application in order to more fully describe the state of the art to which this invention pertains. Although the invention has been described with reference to the exampled provided above, it should be understood that various modifications can be made without departing from the spirit of the invention.

What is claimed is:

1. A cleaning injection port cap, comprising:
   a substantially cylindrical body comprising a passageway extending from a proximate end to a distal end, the proximate end being configured to open for receiving an end portion of a tube to be capped and to close for holding the end portion;
   an actuating member disposed on a middle portion of the body and configured to open only the proximate end of the body by squeezing the actuating member and to close the proximate end of the body by releasing the squeezed actuating member;
   a plurality of separable absorbent elements located within the passageway adjacent the proximal end; and
   a flexible fluid impermeable sheath covering and layered on at least a portion of an exterior of the body.

2. The cleaning injection port cap of claim 1, wherein the absorbent elements are impregnated with an antimicrobial solution.

3. The cleaning injection port cap of claim 1, wherein the absorbent elements form a substantially closed surface when the proximate end is closed.

4. The cleaning injection port cap of claim 1, wherein the absorbent elements are spatially separated from one another when the proximate end is opened.

5. The cleaning injection port cap of claim 1, wherein the proximate end is configured to accommodate a luer fitting disposed at the end portion of the tube when the proximate end is opened.

6. The cleaning injection port cap of claim 1, wherein one or more of the absorbent elements are configured to scrub an exterior of the end portion of the tube as the end portion of the tube is inserted in the proximate end.

7. The cleaning injection port cap of claim 1, wherein the plurality of separable absorbent elements include two substantially half cylindrical sponges, wherein the sponges are adjacent one another when the proximate end is closed and separate from one another when the proximate end is opened.

8. The cleaning injection port cap of claim 1, wherein the body is constructed of a deformable material.

9. The cleaning injection port cap of claim 1, wherein the actuating member comprises at least one squeezing portion protruding radially outward from a major axis of the passageway.

10. The cleaning injection port cap of claim 9, wherein:
    said at least one squeezing portion has a concave portion for fingers to squeeze the actuating member.

11. The cleaning injection port cap of claim 1, wherein the cleaning injection cap further comprises a needleless valve connector for a needleless valve to be attached to the distal end.

12. The cleaning injection port cap of claim 11, wherein a bottom surface of the absorbent element is configured to contact an opening of the needleless valve.

13. The cleaning injection port cap of claim 11, wherein the needleless valve have a luer fitting connector configured to accommodate a luer fitting disposed at the end portion of the tube.

14. The cleaning injection port cap of claim 1, further comprising a luer fitting element, wherein:
    the luer fitting element has a first end and a second end,
    the first end is disposed in the body of the cleaning injection port cap and is configured to accommodate the end portion of the tube, and
    the second end is disposed outside the body of the cleaning injection port cap and is configured to accommodate an end portion of a catheter.

15. The cleaning injection port cap of claim 14, wherein the first end of the luer fitting element has a female screw and the second end of the luer fitting element has a male screw.

16. A cleaning device, comprising:
    a substantially cylindrical body having a cavity and a squeezing position disposed on a middle of the cylindrical body and configured to open only one end of the cleaning device from a closed state when compressed and to close said one end when released; and
    a scrubbing foam disposed in said cavity, the scrubbing foam comprising substantially half cylindrical shaped foams;
    wherein each of said half cylindrical shaped foams has a semicircle fluid impermeable member which prevents a solution from evaporating from said scrubbing foam and faces outward from said cavity when the cleaning device is in the closed state.

17. The cleaning device of claim 16, further comprising an antimicrobial solution dispersed in said scrubbing foam.

18. The cleaning device of claim 16, wherein the scrubbing foam is configured to scrub an exterior of an end portion of a tube as the end portion of the tube is inserted in the cleaning device.

19. The cleaning device of claim 16, further comprising a luer fitting element, wherein:
    the luer fitting element has a first end and a second end,
    the first end is disposed in the body of the cleaning device and is configured to accommodate an end portion of a tube, and
    the second end is disposed outside the body of the cleaning device and is configured to accommodate an end portion of a catheter.

20. The cleaning device of claim 19, wherein the first end of the luer fitting element has a female screw and the second end of the luer fitting element has a male screw.

21. The cleaning device of claim 16, wherein an end portion of the cylindrical body covers a circumference area of the semicircle fluid impermeable member.

* * * * *